(12) United States Patent
Sutcliffe

(10) Patent No.: US 6,805,714 B2
(45) Date of Patent: Oct. 19, 2004

(54) ANCHORABLE VERTEBRAL IMPLANT

(75) Inventor: John Sutcliffe, Good Easter (GB)

(73) Assignee: Ulrich GmbH & Co. KG, Ulm (DE)

(*) Notice: Subject to any disclaimer, the term of this patent is extended or adjusted under 35 U.S.C. 154(b) by 0 days.

(21) Appl. No.: 10/112,892

(22) Filed: Apr. 1, 2002

(65) Prior Publication Data
US 2002/0143399 A1 Oct. 3, 2002

(30) Foreign Application Priority Data
Apr. 2, 2001 (DE) .......................... 101 16 412

(51) Int. Cl.$^7$ .................................. A61F 2/44
(52) U.S. Cl. ..................... 623/17.11; 623/17.15; 623/17.16
(58) Field of Search ................ 623/17.11, 17.15, 623/17.16; 606/61

(56) References Cited

U.S. PATENT DOCUMENTS

| | | | |
|---|---|---|---|
| 5,192,327 A | * 3/1993 | Brantigan | 623/17.11 |
| 5,458,641 A | * 10/1995 | Ramirez Jimenez | 623/17 |
| 5,571,192 A | 11/1996 | Schonhoffer | |
| 5,702,455 A | * 12/1997 | Saggar | 623/17.15 |
| 5,776,198 A | * 7/1998 | Rabbe et al. | 623/17 |
| 5,888,223 A | 3/1999 | Bray, Jr. | |
| 5,916,267 A | * 6/1999 | Tienboon | 623/17 |
| 5,989,290 A | * 11/1999 | Biedermann et al. | 623/17 |
| 6,190,413 B1 | * 2/2001 | Sutcliffe | 623/17.11 |
| 6,228,118 B1 | * 5/2001 | Gordon | 623/17.14 |
| 6,296,664 B1 | * 10/2001 | Middleton | 623/17.15 |
| 6,296,665 B1 | * 10/2001 | Strnad et al. | 623/17.16 |
| 6,432,106 B1 | * 8/2002 | Fraser | 606/61 |

FOREIGN PATENT DOCUMENTS

| | | | |
|---|---|---|---|
| DE | 41 09 941 | 10/1992 | |
| DE | 4423257 | 1/1996 | |
| DE | 19826619 | 6/1998 | |
| DE | 19816782 A1 | * 10/1999 | .......... A61B/17/70 |
| EP | 0302719 | 8/1989 | |
| EP | 0 560 140 | 9/1993 | |
| EP | WO-97/20526 | 6/1997 | |
| FR | 2727003 | 11/1994 | |
| WO | WO 99/56675 | 11/1999 | |
| WO | WO 99/63913 | 12/1999 | |
| WO | WO 01/15637 | 3/2001 | |

OTHER PUBLICATIONS

Messerli et al. Pub. No. US 2002/0099443 A1, Pub. Date Jul. 25, 2002, End Member for a Bone Fusion Implant.*
Boyer, II et al. Pub. No. US 2002/0056302 A1, Pub. Date Mar. 22, 2001, Skeletal Reconstruction Cages.*

* cited by examiner

Primary Examiner—Bruce Snow
Assistant Examiner—Cheryl Miller
(74) Attorney, Agent, or Firm—Herbert Dubno

(57) ABSTRACT

A spinal implant for engagement in a space between upper and lower vertebrae has a center part extending along an axis and formed with upper and lower screwthreads of opposite hand. Respective upper and lower end parts axially flank the center part and each have an inner end threaded onto a respective one of the screwthreads and an outer end adapted to bear on a respective one of the vertebrae. One of the end parts is formed with an eye having a hole open transversely of the axis. A screw engages through the hole and anchors the one end part to the respective vertebra. The other end part is also formed with an eye having a hole open transversely of the axis and another screw engages through this hole and anchors the other end part to the respective vertebra.

13 Claims, 5 Drawing Sheets

ANCHORABLE VERTEBRAL IMPLANT

FIELD OF THE INVENTION

The present invention relates to a vertebral implant. More particularly this invention concerns such an implant used to replace one or vertebrae and/or intervertebral disk.

BACKGROUND OF THE INVENTION

When a vertebra is broken or crushed it is frequently necessary to ablate the body of the crushed or broken vertebra or vertebra as well as any damaged intervertebral disk. In order, however, to prevent the spinal column from collapsing with damage to the fragile spinal cord running in the vertebral foramen forward of the vertebral body, it is necessary to implant a spacer. This implant is braced vertically between the bodies of the adjacent vertebra and holds them apart at the desired spacing.

In commonly owned U.S. Pat. No. 5,571,192 a spinal implant is described having a tubular center part extending along an axis and a pair of end parts. The center part is formed with upper and lower screwthreads of opposite hand and with a plurality of radially throughgoing apertures. The upper and lower tubular end parts are each formed with a plurality of radially throughgoing apertures, each have a circular-section inner end threaded onto a respective one of the screwthreads, and each have an outer end adapted to bear on a respective one of the adjacent vertebrae.

Such an implant is highly effective. Nonetheless its installation is somewhat tricky until it has been expanded into place so that the two end parts bite into the respective vertebrae. In addition the entire implant area is not stable until there has been substantial bone growth around and through the implant, so that the patient must be very careful to avoid any displacement of the implant before it sets fully.

OBJECTS OF THE INVENTION

It is therefore an object of the present invention to provide an improved vertebral implant.

Another object is the provision of such an improved vertebral implant which overcomes the above-given disadvantages, that is which can be solidly anchored in place.

SUMMARY OF THE INVENTION

A spinal implant for engagement in a space between a pair of adjacent vertebrae has according to the invention a center part extending along an axis and formed with upper and lower screwthreads of opposite hand. Respective upper and lower end parts axially flank the center part and each have an inner end threaded onto a respective one of the screwthreads and an outer end adapted to bear on a respective one of the adjacent vertebrae. One of the end parts is formed with an eye having a hole open transversely of the axis. A screw engages through the hole and anchors the one end part to the respective vertebra. Normally in accordance with the invention the other of the end parts is also formed with an eye having a hole open transversely of the axis and another screw engages through the hole of the other end part and anchors the other end part to the respective vertebra.

Thus it is possible to anchor the implant solidly to the spine. The cortical screws engage well into the respective vertebrae so that the implant is not only held in place by engagement of upper and lower normally toothed faces of the end parts in the overlying and underlying vertebrae, but also by these screws. The result is a solid uniting of the implant to the two flanking vertebrae. Thus even if considerable torque is exerted on the center part to distract these vertebrae, the end parts will stay put.

The ability to anchor both end parts to the respective vertebrae is particularly advantageous when accommodating certain installations. For example when the implant is to be installed at the lower end of the vertebrae above the sacral vertebrae, it is advantageous to be able to work from above, with screws angled down through the lower element into the sacrum. Thus the operating field can be small. Furthermore the implant lies wholly between the vertebrae it is mounted between, within the vertical projection of the spine so that it can be left in place and the operating wound can be closed and left closed.

The eye of the other end part according to the invention is formed as a tab extending generally parallel to the axis so that its hole and the screw through it is generally perpendicular to the axis.

In another arrangement the eye is open at an acute angle away from the other part and is thickened. Normally the eye is open at an angle of between 25° and 65° to the axis, preferably 45°.

The eye according to the invention is unitarily formed with the one end part. In addition the inner ends are formed as axially extending stems and the center part is a sleeve threaded over the stems. In addition the parts are formed with radially open throughgoing holes so that bone can grow into and through the parts. These parts can be made of titanium, a biocompatible plastic, ceramic, or bone.

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
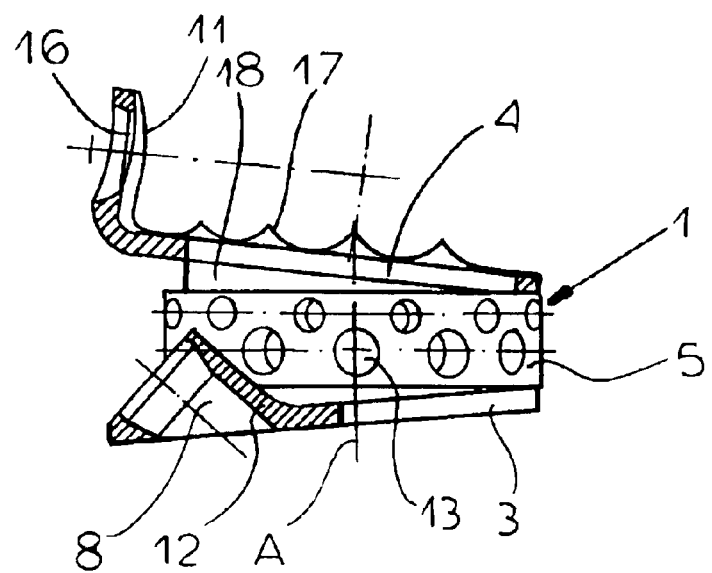
FIG. 1 is a side view partly in vertical section through the implant according to the invention.
Figure 2:
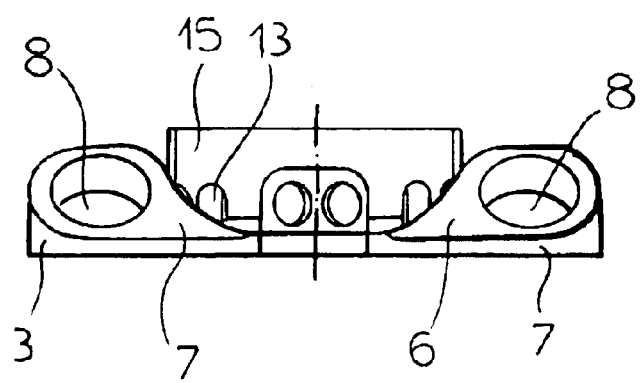
FIG. 2 is a front view of the bottom part of the implant.
Figure 3:
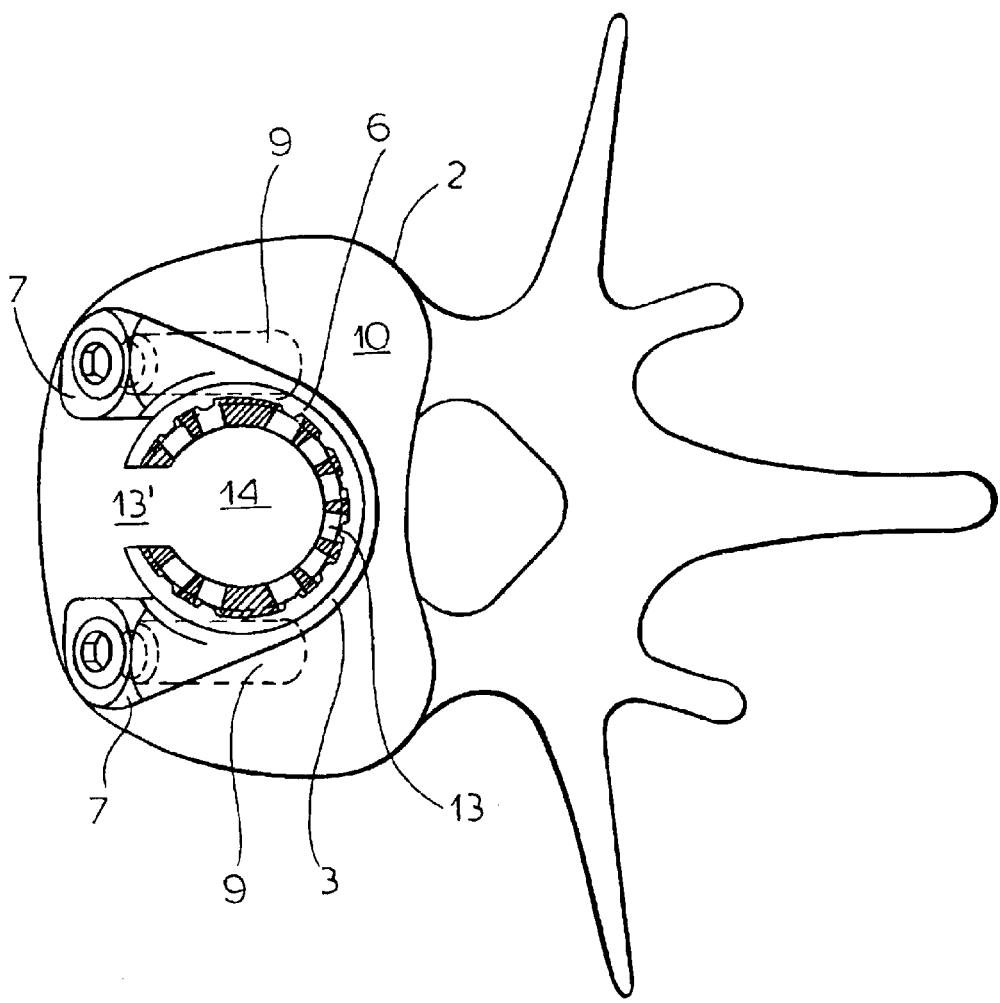
FIG. 3 is a horizontal section through the implant when installed.

As seen in FIGS. 1 and 2 an implant 1 according to the invention for installation between a pair of vertebrae 2 has a lower end part 3, and upper end part 4, and a center sleeve or part 5, all made of a biologically inert or absorbable material such as steel, titanium, bone, bioceramic, or polyetherether-ketone (PEEK). The upper part 2 has a downwardly extending externally threaded tubular stem 18 and the lower part 3 has an upwardly extending externally threaded tubular stem 15. The screwthreads of the stems 15 and 18 are of opposite hand and mate with complementary screwthreads in the sleeve part 5 so that rotation in one direction relative to a center axis A will spread the parts 3 and 4 vertically and distract the vertebrae 2 and opposite rotation will move them together. The upper and lower surfaces of the parts 3 and 4 can be parallel to each other but are normally inclined at a slight acute angle to each other, making the implant 1 wedge shaped to correspond to the normal lordosis of the spine.

The parts 3 and 4 are formed with radially throughgoing holes 13 and with an axially extending slot 13' so that an interior 14 can be packed with bone chips and so that bone growth through the implant 1 is possible. In addition the parts 3 and 4 have lower and upper surfaces formed with teeth 17 that bite into the respective end surfaces 10 of the vertebrae 2 to prevent the implant 1 from slipping.

Figure 6:
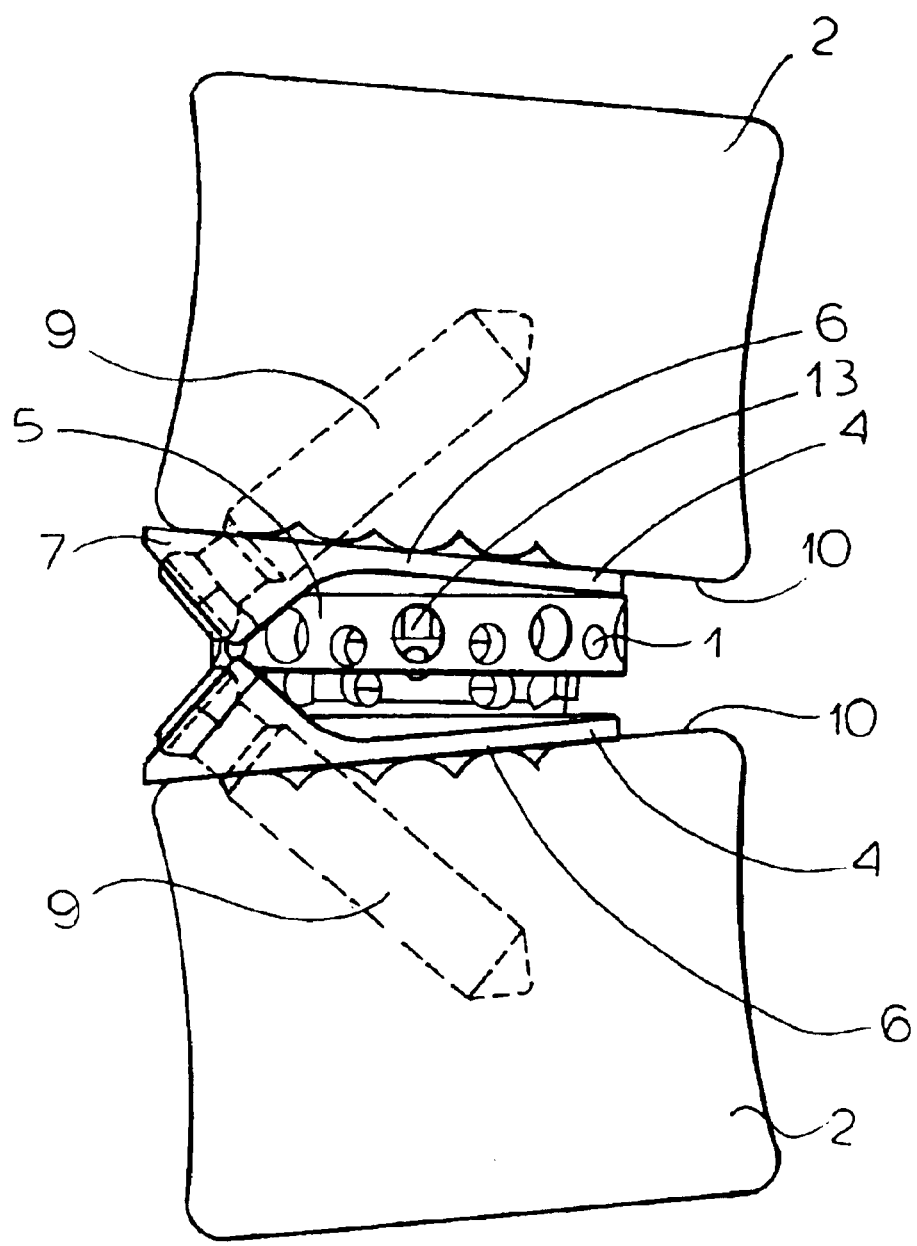
FIG. 6 is a view like FIG. 4 of another implant in accordance with the invention.

According to the invention the lower part 3 is unitarily formed with a pair of eyes 6 having collars 7 defining holes or passages 8 with cylindrical inner surfaces 12 extending at an acute angle of between 25° and 65° to the lower vertebral surface 10, here 45°. Cortical screws 9 extend through these eyes 6 and into the lower vertebra 2 to solidly anchor the lower part 3 to the lower vertebra 2. FIG. 6 shows how a similar pair of eyes 6 can be formed on the upper end part 4 in an arrangement allowing the implant 1 to be installed through a very small surgical opening.

Figure 4:
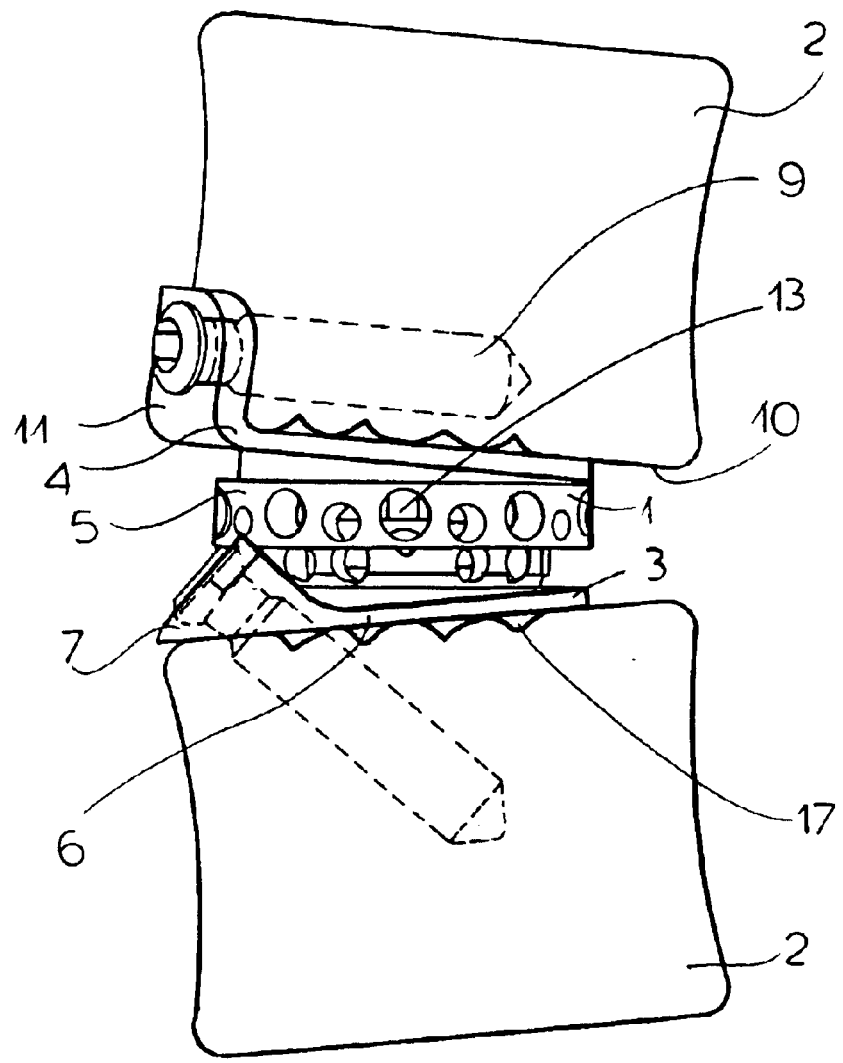
FIG. 4 is a side view of the installed implant.
Figure 5:
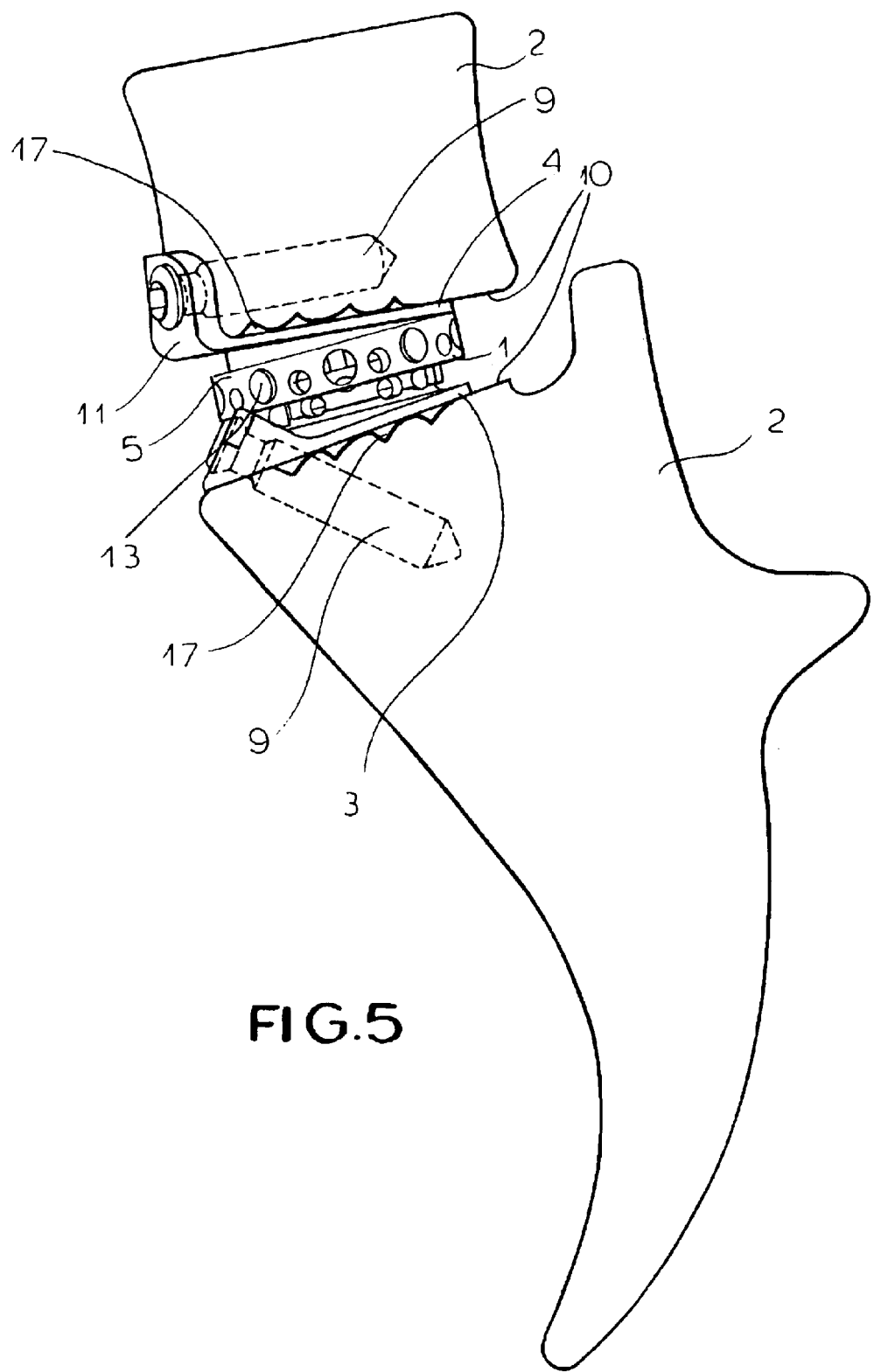
FIG. 5 is a view like FIG. 4 but with the implant installed in the caudal area of the spine.

In FIGS. 1, 4, and 5 the upper part 4 has a pair of bent-up tabs or flanges 11 formed with openings 16 extending parallel to the upper vertebral surface 10. Cortical screws 9 extend perpendicular to the axis A through the openings 16 to anchor the upper part 4 to the upper vertebra 2.

Thus with this system, after the disk or vertebra has been ablated, the implant 1 is set in position and the sleeve part 5 is rotated to press the teeth 17 lightly into the lower and upper surfaces of the vertebrae above and below the implant. Then pilot holes are drilled in line with the holes 8 and 16 and cortical screws 9 are threaded through them into the vertebrae 2, anchoring the implant 1 solidly in place. The sleeve 5 can then be rotated further to achieve the desired level of distraction, and the operating field is closed.

I claim:

1. A spinal implant for engagement in a space between upper and lower vertebrae, the implant comprising:
   a center part extending along an axis and formed with upper and lower screwthreads of opposite hand;
   respective upper and lower generally annular end parts axially flanking the center part and each having an inner end threaded onto a respective one of the screwthreads and an outer end adapted to bear on a respective one of the vertebrae, the end parts each being formed with a radially and axially throughgoing slot, each of the end parts further being unitarily formed with two generally axially projecting tabs forming eyes flanking the respective slot and each forming a hole open transversely of the axis, the slots being sufficiently wide that bone chips can be inserted radially into interiors of the end parts and center parts through the slots; and
   respective screws engaged through the holes for anchoring the end parts to the respective vertebrae.

2. The spinal implant defined in claim 1 wherein the tabs extend generally parallel to the axis.

3. The spinal implant defined in claim 1 wherein the eyes of the end parts are open at an acute angle away from the respective center and end parts.

4. The spinal implant defined in claim 3 wherein the eyes tabs are thickened.

5. The spinal implant defined in claim 3 wherein the eyes are open at an angle of between 25° and 65° to the axis.

6. The spinal implant defined in claim 4 wherein the eyes are open at an angle of about 45° to the axis.

7. The spinal implant defined in claim 1 wherein the inner ends are formed as axially extending stems and the center part is a sleeve threaded over the stems.

8. The spinal implant defined in claim 7 wherein the stems carry screwthreads of opposite hand.

9. The spinal implant defined in claim 1 wherein the eyes are open at an acute angle to the axis.

10. The spinal implant defined in claim 1 wherein the end parts have outer faces formed with teeth for engaging the respective vertebrae.

11. The spinal implant defined in claim 1 wherein the end parts are formed with radially open throughgoing holes, whereby bone can grow into and through the parts.

12. The spinal implant defined in claim 1 wherein the end parts are of titanium.

13. The spinal implant defined in claim 1 wherein the end parts are of a biocompatible plastic, ceramic, or bone.

* * * * *